United States Patent
Thornton

(10) Patent No.: US 6,406,438 B1
(45) Date of Patent: Jun. 18, 2002

(54) METHOD AND APPARATUS FOR OBTAINING EVOKED OTOACOUSTIC EMISSIONS

(75) Inventor: Arthur Roger David Thornton, Bitterne (GB)

(73) Assignee: Medical Research Counsel, London (GB)

( * ) Notice: Subject to any disclaimer, the term of this patent is extended or adjusted under 35 U.S.C. 154(b) by 0 days.

(21) Appl. No.: 09/555,918

(22) PCT Filed: Dec. 17, 1997

(86) PCT No.: PCT/GB98/03789

§ 371 (c)(1),
(2), (4) Date: Jun. 6, 2000

(87) PCT Pub. No.: WO99/32989

PCT Pub. Date: Jul. 1, 1999

(30) Foreign Application Priority Data

Dec. 19, 1997 (GB) .............................................. 9726711

(51) Int. Cl.[7] .................................................. A61B 5/00
(52) U.S. Cl. ...................................................... 600/559
(58) Field of Search .................... 600/559; 381/312–331

(56) References Cited

U.S. PATENT DOCUMENTS 5,734,827 A * 3/1998 Thornton et al. ............ 395/200

FOREIGN PATENT DOCUMENTS

WO     WO 93/19670    10/1993

OTHER PUBLICATIONS

Thornton, "Technical Aspects of Recording Evoked Otoacoustic . . . ", Scandinavian Audiology, vol. 23, No. 4, 1994, pp. 225–231.

Deltenre, "Temporal distortion products (kernal slices) . . . " Electroencephalography, vol. 104, No. 1, 1/97, pp. 10–16.

Shi, "Nonlinear System Identification by M–Pulse Sequences . . . ", IEEE, vol. 38, No. 9, 9/91, pp. 834–845.

Shi, "The use of M–Pulse Sequences in the Study of Monlinearities . . . ", IEEE Proceedings, vol. 11, No. 4/6, 11/8–12/89, pp. 1289–1290.

Dunn, "Distortion Immunity of MLS–Derived Impulse Response Measurements", Journal of AES, vol. 41, No. 5, 5/93, pp. 314–355.

Greest, "Distortion Analysis of nonlinear systems with memory using maximum–length sequences", IEEE Proceedings, vol. 142, No. 5, 10/95, pp. 345–350.

* cited by examiner

Primary Examiner—Kevin Shaver
Assistant Examiner—Pamela P. Wingood
(74) Attorney, Agent, or Firm—Lee, Mann, Smith, McWilliams, Sweeney & Ohlson

(57) ABSTRACT

A method of obtaining evoked otoacoustic emission (EOAE) response data, wherein stimulus and response signals in the form of a maximum length sequence (MLS) are deconvolved immediately and the non-linear interaction components (NLTICs) in the response data are detected, preferably by cross-correlation of a stimulus sequence and a response sequence.

7 Claims, 7 Drawing Sheets

JH:E1L70R1000O2S2

$$y(t) = \int_{-\infty}^{\infty} h_1(\tau)x(t-\tau)d\tau$$

$$+ \int_{-\infty}^{\infty}\int_{-\infty}^{\infty} h_2(\tau_1,\tau_2)x(t-\tau_1)x(t-\tau_2)d\tau_1 d\tau_2$$

$$+ \int_{-\infty}^{\infty}\int_{-\infty}^{\infty}\int_{-\infty}^{\infty} h_3(\tau_1,\tau_2,\tau_3)x(t-\tau_1)x(t-\tau_2)x(t-\tau_3)d\tau_1 d\tau_2 d\tau_3$$

$$+ \ldots$$

Figure 1

$$k(t) = h(t) - \frac{1}{L}\sum_{i=0}^{L-1} h(i),$$

Figure 2

$$\Phi_{bb}(m) = \begin{cases} 1 & \text{if } m = kL,\ k \in \{0,1,2,\ldots\} \\ -\dfrac{1}{L} & \text{otherwise.} \end{cases}$$

Figure 3

$$c(n) = \begin{cases} b(i) & \text{if } n = qi,\ q \in \{0,1,2,\ldots\} \\ 0 & \text{otherwise} \end{cases}$$

Figure 4

$$\Phi_{cc}(m) = \begin{cases} 1 & m = kL \\ -\dfrac{1}{L} & m = qi \\ 0 & \text{otherwise.} \end{cases}$$

Figure 5

$$s(n) = \begin{cases} 1-b(i) & n = iq \\ 0 & \text{otherwise} \end{cases}$$

$$r(n) = \begin{cases} -b(i) & n = iq \\ 0 & \text{otherwise.} \end{cases}$$

Fig. 6

$$\Phi_{sr}(m) = \begin{cases} \dfrac{L+1}{L} & m = kL \\ 0 & \text{otherwise.} \end{cases}$$

Fig. 7

$$\Phi_{sr}(m) = \begin{cases} \dfrac{L+1}{2L} & m = kL \\ 0 & \text{otherwise.} \end{cases}$$

Fig. 8

$$\Phi(m) = \frac{L+1}{4L}\sum_{\substack{k=-l \\ k\neq 0}}^{l} h_2(m, m+k) + \frac{L+1}{4L}\sum_{\substack{k=-l \\ k\neq 0}}^{l} h_2(m-k, m)$$
$$-\frac{L+1}{4L}\sum_{\substack{k=-l \\ k\neq 0}}^{l} h_2(m-f(k), m-f(k)+k)$$
$$+\frac{L+1}{2L} h_2(m,m) + \frac{1}{2} h_1(m).$$

Fig. 9

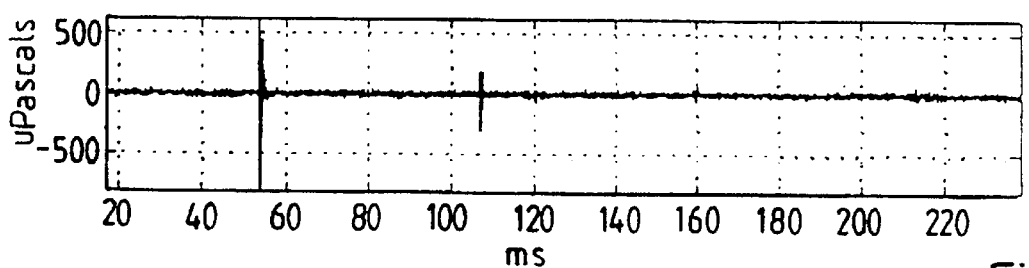

Fig. 10

JH:E1L70R100002S2  (5-20 ms)
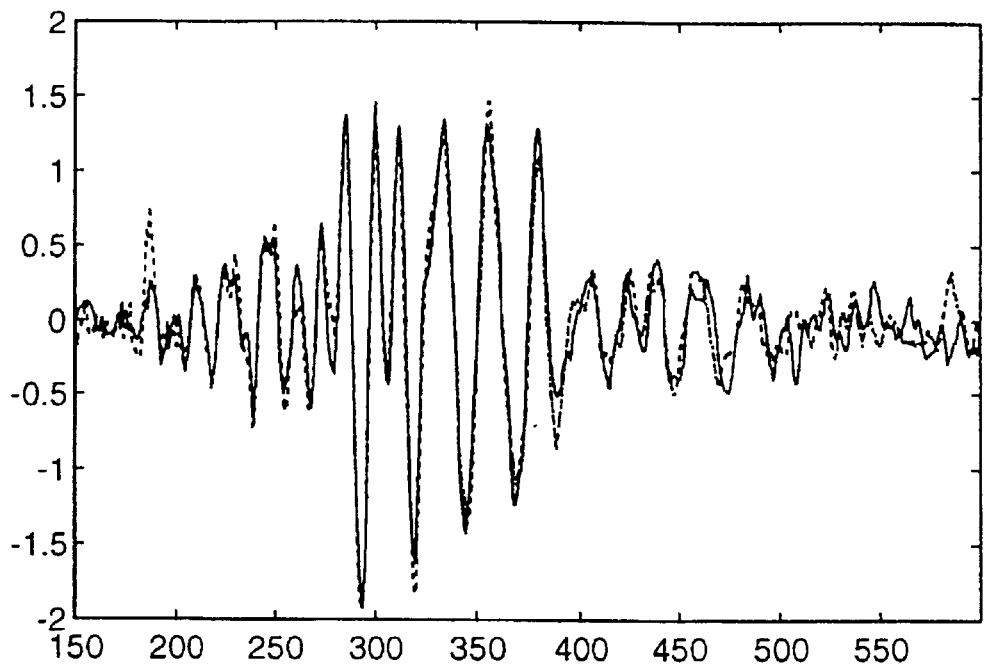
JH:E1L70R100003S2  (5-20 ms)
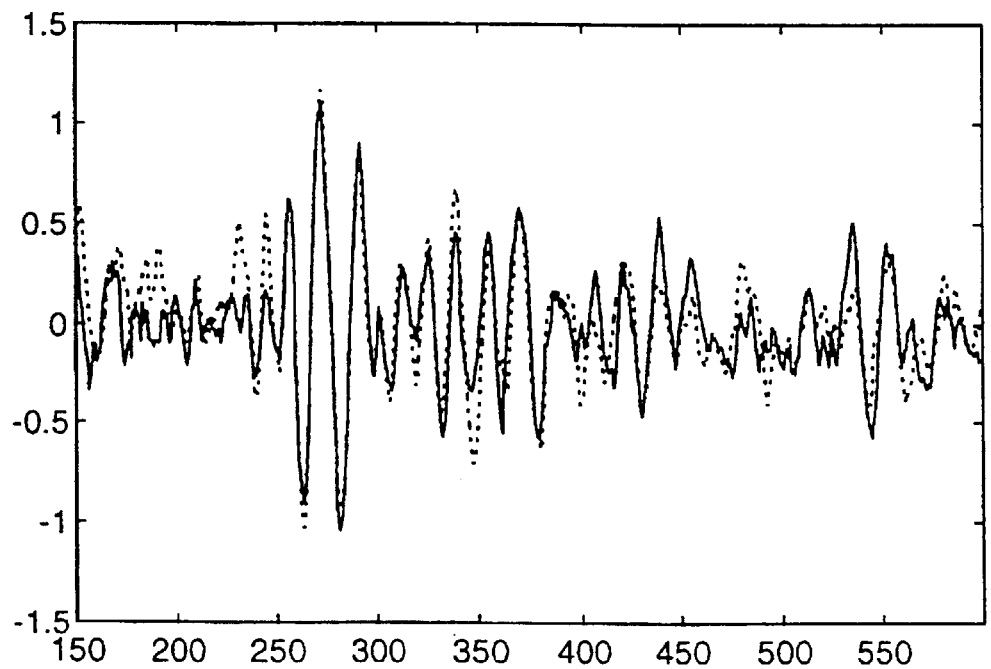
FIGURE12

METHOD AND APPARATUS FOR OBTAINING EVOKED OTOACOUSTIC EMISSIONS

This invention relates to a method of and apparatus for obtaining evoked otoacoustic emission response data by deconvolving stimulus and response signals in the form of maximum length sequences (MLS). References herein to MLS are intended to include similar sequences or variants of similar sequences.

Much previous audiological research has been forced, through technological and intellectual limitations, to make the assumption that the cochlea is time-invariant and linear. There is now much evidence that this is not so. There is also an increasing awareness that non-linearities are the key to important aspects of normal auditory function and that some of the non-linear components may reflect auditory dysfunction more sensitively than the linear components previously studied.

The applicants' published specification WO 94/25925 discloses deconvolution of MLS response data to detect otoacoustic emissions. Such a known technique is applicable to situations in which, for both research and clinical practice, it is an advantage to obtain the emission very quickly. If one tries to speed up the process by increasing click presentation rates, the responses would overlap both each other and the stimulus clicks for rates greater than about 50 clicks/s. It would be impossible to recover the normal evoked emission from these overlapped recordings. However, if a particular sequence of clicks and silences, known as a maximum length sequence, is presented, then the overlapped responses may be deconvolved to give the original response that would have been obtained from conventional averaging.

Hence, previous work has shown that it is possible to obtain an otoacoustic emission response by deconvolving an MLS stimulus. As the stimulus rate is increased, non-linear temporal interaction components (NLTICs) are produced because of the non-linear nature of the auditory system, and the invention results from work carried out to identify and record NLTICs.

According to one aspect of the invention there is provided a method of obtaining evoked otoacoustic emission (EOAE) response data by deconvolving stimulus and response signals in the form of a maximum length sequence (MLS), comprising detecting non-linear temporal interaction components (NLTICs) in the response data.

Preferably, the response data is recorded in real time.

For both evoked otoacoustic emissions (EOAEs) and evoked potentials (EPs), three types of non-linearity can be distinguished:

(a) the non-linear growth of response amplitude with increasing stimulus level;

(b) the frequency domain non-linear distortion products that occur when two tones are used as the stimulus and which may be seen as combinations of sum and difference tones; and (c) non-linear temporal interaction, which creates an increase in the non-linear activity as the time between stimuli decreases.

Types (a) and (b) have been described in the prior art. In simple systems without memory, (b) can be derived from (a). However, the cochlea is a non-linear system with memory and incorporates interactions between different frequency elements. Such a system can have non-linearities of types (a), (b) and (c), none of which can be well predicted from the others. For example, the type (c) non-linearities arise essentially out of the interactions between responses to stimuli juxtaposed in time, irrespective of the non-linear input/output function of the EOAE.

A linear system can be characterised by its impulse response and, for any input to the system, the output may be calculated by convolving the input with the system's impulse response. However, more information is needed to define a non-linear system. If the input to a non-linear system is an MLS, then the output may be expressed as a Volterra series in which the elements are known as "kernels". The first order kernel represents the convolution of the impulse response with the input; ie, it defines the output in exactly the same way as it is defined in a linear system and it is sometimes referred to as the "linear component" of the series. The second order kernel is 3-dimensional (amplitude×time for click 1×time for click 2) and represents the convolution of all possible non-linear interactions created by pairs of stimuli. The third order kernel is 4-dimensional (amplitude×time for click 1×time for click 2×time for click 3) and represents the convolution of all possible non-linear interactions caused by triples of stimuli.

Because the MLS is a discrete, digital input, the kernels are defined only at intervals which are a multiple of the minimum inter-stimulus interval of the MLS. Each of these segments of the kernel is known as a slice. When the MLS is deconvolved, the slices from the various kernels are scattered along the entire deconvolved MLS waveform. The slices have to be extracted and combined to estimate the kernels. In this way the temporal non-linearities of the system can be characterised by a Volterra series and the individual elements described by the Volterra kernel slices. Previously, this type of approach had been carried out only for auditory brainstem responses (ABRs), where it appeared that two or three major components were sufficient to adequately represent the non-linear behaviour of the system.

Thus, in accordance with a further feature of the invention, the non-linear temporal interaction components may be recorded as slices through higher order Volterra kernels, with each Volterra kernel representing a term in a Volterra series which models the stimulus/response system. The Volterra series gives information on the linear components and also the second and higher order non-linear components, and it is the second and higher order components with which the invention is principally concerned.

The location of the NLTIC slices is very hard to predict. For any particular MLS they may occur anywhere within that MLS, even overlapping each other and the linear component at the start of the MLS.

In order accurately to record the linear and the NLTICs for each order of MLS, all possible MLSs had to be generated and the location of the NLTICs computed. The "optimum" MLS is the one that has the minimum overlap between these NLTICs with each other and with the linear component at the start. Following this computation the optimum MLSs were defined for each order of MLS.

Special software was written to implement these MLSs and to record the otoacoustic emissions. It was not known whether otoacoustic emissions would show these NLTICs but, in the event, they did.

The identification of these components and the knowledge of any overlap is possible only because of the extensive computation carried out on all possible combinations of MLS.

The computation of the position of each slice in the recovered MLS may be computed so that each slice can be properly identified.

According to another aspect of the invention there is provided apparatus for obtaining evoked otoacoustic emission (EOAE) response data by deconvolving stimulus and response signals in the form of a maximum length sequence (MLS), comprising means for detecting non-linear temporal interaction components (NLTICs) in the response data.

Mathematically an MLS is a pseudo-random sequence of −1s and +1s. Its auto-correlation function is 1 for 0 lag and otherwise is −1/L, which is also its average value.

The particular variant of MLS that has been developed for use in evoked response recording is obtained by replacing the −1s with +1s and the +1s with 0s. The +1 represents a click stimulus and the 0 represents silence. In practice, evoked response recordings require the rejection of noisy epochs so that they do not add to the average and worsen the signal-to-noise ratio. Now, with MLS stimulation for OAEs, there are stimuli occurring at intervals as small as 200 μs. Thus it is impossible to apply the normal rejection template to detect noisy epochs. It was therefore considered important to develop a technique in which the deconvolution of the MLS was carried out "on-the-fly" as the MLS was being generated. Thus, at the end of the first MLS, there would be a deconvolved waveform to which the normal rejection template could be applied. In addition, whilst the second MLS was being acquired and deconvolved into a separate buffer, the deconvolved waveform from the first buffer could be withheld from or added to the average dependent on the rejection criteria.

For such a system to be implemented a reconstruction technique is needed that would work in real time. Thus, a recovery sequence was created comprising +1 when the MLS was +1 and −1 when the MLS was 0. It can easily be shown that, at least for the linear component of the response, a very much simpler algorithm, usable in real time, can replace the correlation procedure to recover the response.

Consider an order 2 MLS, 1,1,0 with its recovery sequence 1,1,−1. The recovery process can be carried out by zeroing a buffer area and then obeying the following rules.

If the element in the recovery sequence, corresponding to the left hand element in the MLS, is a −1, then invert the MLS and add it to the buffer.

Rotate the original MLS one place to the left.

Repeat this procedure until the number of rotations completed is one less than the length of the MLS.

Thus, for the MLS variants used in this study, the recovery can be carried out in real time enabling the rejection of noisy epochs.

In the accompanying drawings:

FIGS. 1 to 9 show mathematical expressions; and

FIGS. 10 to 15 are graphs showing results.

Figure 11:
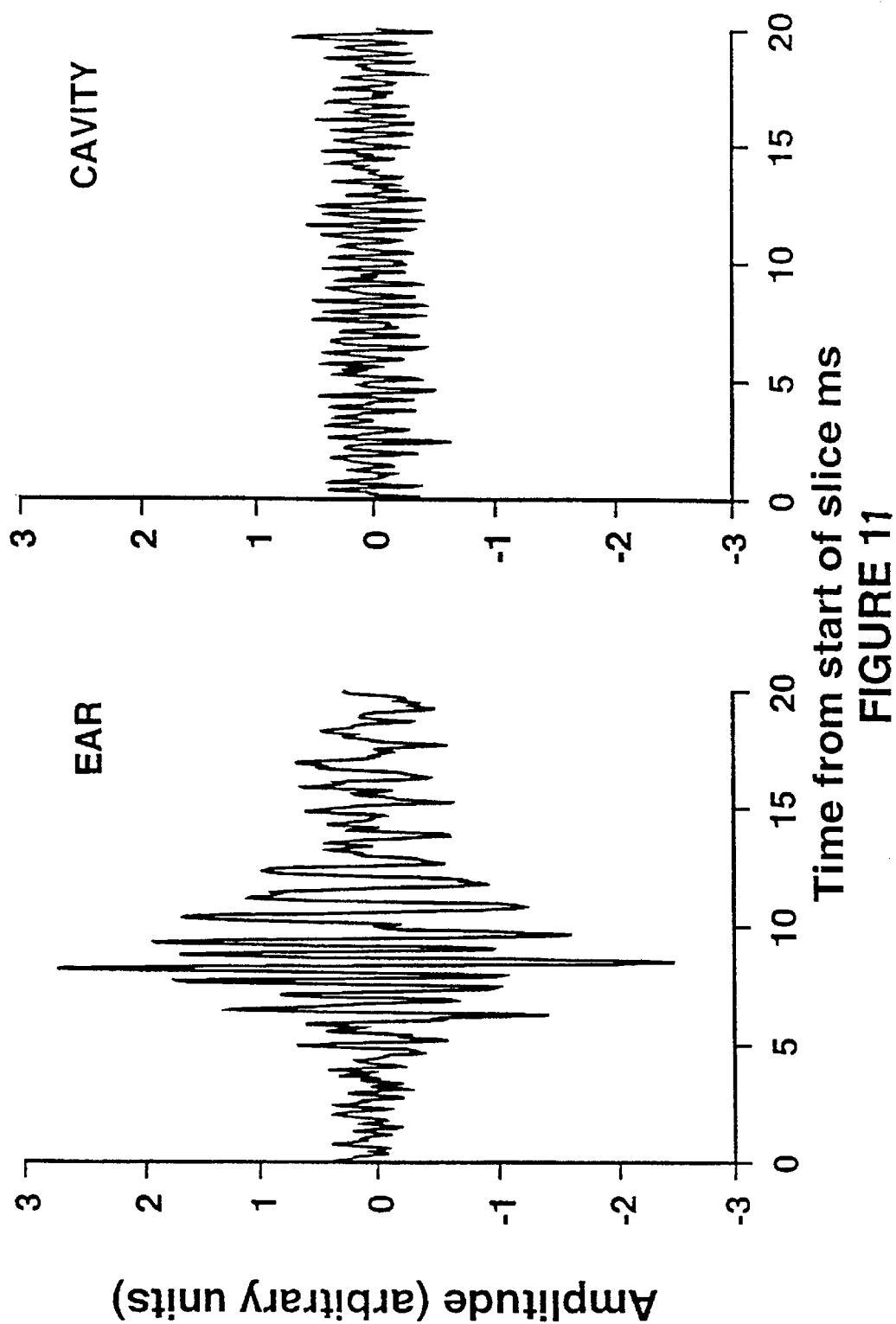

The Volterra series is one way of modelling non-linear systems. It is expressed mathematically by the expression of FIG. 1, where x(t) is the input and y(t) is the output. The functions $h_1(\tau)$, $h_2(\tau_1, \tau_2)$ and $h_3(\tau_1, \tau_2, \tau_3)$ are called the Volterra kernels. Identifying these kernels identifies the system in a similar way that identifying the system impulse response identifies a linear system. Note that a linear system is identified by the first order Volterra kernel. The kernels are recovered by a correlation procedure which is detailed later.

Otoacoustic emissions are known to be rate dependent, that is the properties of the emission vary with the speed of the clicks evoking it and a computer model with this type of non-linearity has been written. This model has shown that the Volterra series is suitable for characterising rate-dependent non-linearities.

Hitherto the Volterra series model has not been much used due to the difficulty of identifying the higher order kernels from the output y(t). However, it has been shown that a maximum length sequence as input does allow information about kernels higher than first order to be recovered. This section contains details of how this recovery works as sell as information on the modified form of MLS that is used in practice. For the sake of clarity much of the development that follows will be in terms of a linear system so that any error terms will be clearly shown up.

A standard way of identifying linear systems is to use a delta function, that is an infinitely narrow, infinitely high impulse, as an input. In this case the output is the system impulse response function h(t) and no further recovery is needed. A delta function is approximated in real life by a click, and it is a stream of positive and negative clicks that makes up the MLS.

For an MLS input the recovery is performed by cross-correlating the output with the input, to give a function k(t) which approximates h(t), shown in the expression of FIG. 2, where L is the length of the MLS. The amount by which this estimate deviates from h(t) is the error term and the way in which it arises can be seen if we look at the autocorrelation of an MLS b(n) with itself, as shown by the expression of FIG. 3. It is the non-zero value for $O_{bb}(m)$, $m \neq kL$ that is causing the error and instead of the delta function that we should get, we obtain a delta function with a DC shift.

The situation becomes worse when we take ADC samples between the points of the MLS, which we need to do to avoid aliasing errors. This effectively introduces zeros between the points of the MLS, and causes a wiggle in the resulting correlation. If we call this new sequence c(n) and define it by the expression of FIG. 4 then the autocorrelation is the expression of FIG. 5. These wiggles are of sufficient magnitude to introduce distortions in the linear response, and would make recovering higher order kernels very difficult.

This problem was overcome by defining two new functions, a stimulus sequence s(n) and a recovery sequence r(n).

These sequences can be related to an MLS by the expression of FIG. 6.

Crosscorrelating these two sequences gives the expression of FIG. 7.

This gives a scaled delta function with no wiggle despite the samples between the sequence points.

However, in order to use the techniques of rotating an array and adding it to a buffer as the equivalent of correlation, so that the correlation can be carried out in real time the sequences used have to be +1s and 0s for the stimulus with a recovery sequence of +1s and −1s. In this case the autocorrelation is given by the expression of FIG. 8.

Once more this gives a scaled delta function with all other points being zero.

The rotate and add algorithm actually used in the software for recovery of the linear component has been shown to be mathematically identical to correlation for the stimulus and recovery sequences defined above. This means that it preserves the aspects of the input and recovery sequences that allow extraction of information about higher order kernels. Work is currently going on extracting the second order kernel $h_2(\tau_1, \tau_2)$. Stimulating a system consisting of a first (linear) term and a second order term, and performing the recovery gives the expression of FIG. 9.

Here L is the length of the MLS as before and l is any value after which $h_2$ is zero. The information that is recovered about the second order kernel is contained in the term involving f(k). This term takes diagonal slices out of the second order kernel and places them along the recovered time history. Exactly where they are placed is determined by the function f(k), which is called the offset function and is unique to each particular MLS. Some sequences will place non-linear components in places where they may overlap each other or even overlap the linear component at the beginning of the recovered record. Thus all the possible MLSs up to order 15 have been generated and examined and those which maximally separate the non-linear components have been selected.

In order to be able to measure the Volterra kernel slices contained in the MLS record, the recording system non-linearities must be much smaller in amplitude or much shorter in duration than the physiologically generated non-linearities, Thus, the current stage of this work is to obtain recordings using a 2 cc cavity and so evaluate the non-linearities of the recording system.

FIG. 10 of the accompanying drawings shows the 18–145 ms portion of an order 11 (length 2047) MLS. The recording was made using a 2 cc cavity and click stimulation. The presence of non-linear elements, generated by the click stimulus can be seen. It is not yet known whether these components will be smaller than the physiological ones but they should be significantly shorter, enabling any physiological non-linear components to be measured.

As will be clear from the preceding description, a particular variant of the MLS was used to enable the development of the "on-the-fly" deconvolution technique which is essential to the practical application of the method.

Theoretical and modelling studies have shown that the variant of MLS that we used to provide real-time deconvolution does permit the extraction of information about higher order kernels. Thus, a rigorous scientific foundation has been established for the Volterra kernel measurement.

The "slices" of the Volterra kernels appear as waveforms at various places in the recovered MLS. Some MLSs will place these "slices" in places where they may overlap each other or even overlap the linear component at the beginning of the recovered record. Therefore, all the possible MLSs up to order 15 have been generated and examined to select those which maximally separate the non-linear components. The extremely lengthy theoretical work and computational procedures that this involved have enabled us to optimise the technique.

We have recorded slices of Volterra kernels from adults and neonates. The data obtained have shown: NLTICs do exist in OAEs and are highly repeatable. The Volterra kernel components recorded from real ears differ from the system non-linearities that are recorded in a cavity. The system non-linearities may be distinguished from physiological non-linearities as the physiological responses are of a longer duration. The NLTICs have been found in all subjects tested so far and vary between subjects in a similar way to the linear component of the OAE.

Unlike the published ABR data, OAEs contain a very large number of NLTICs, including many elements from fourth and higher order kernels. This is a mixed blessing in that the presence of many components in the kernels indicate that the cochlea is indeed a non-linear system and the above-described approach to investigate it is correct. On the other hand, very few components would greatly ease the task of analysis and make the realisation of the practical recording system relatively simple.

We have shown that the Volterra kernel approach is applicable to the cochlea, justifying further studies. The data show that the ear is a "weakly non-linear system" of the type that can be described by a Volterra series and so it should be possible to provide a very good predictive model of cochlear function with this approach.

Results achieved by use of the invention are now described with reference to FIGS. 11 to 15 of the accompanying drawings.

FIG. 11 shows the second order, second slice of a Volterra kernel recorded at 1000 clicks/s both in an ear and in an artificial cavity. The difference between the real ear and the cavity recordings demonstrates that this is a physiological response that is clearly measurable despite the presence of any system non-linear interactions.

FIG. 12 shows repeats of the second order, second slice component and, below, the third order, second slice component. The repeats shown the data are highly repeatable within a test session.

Figure 13:
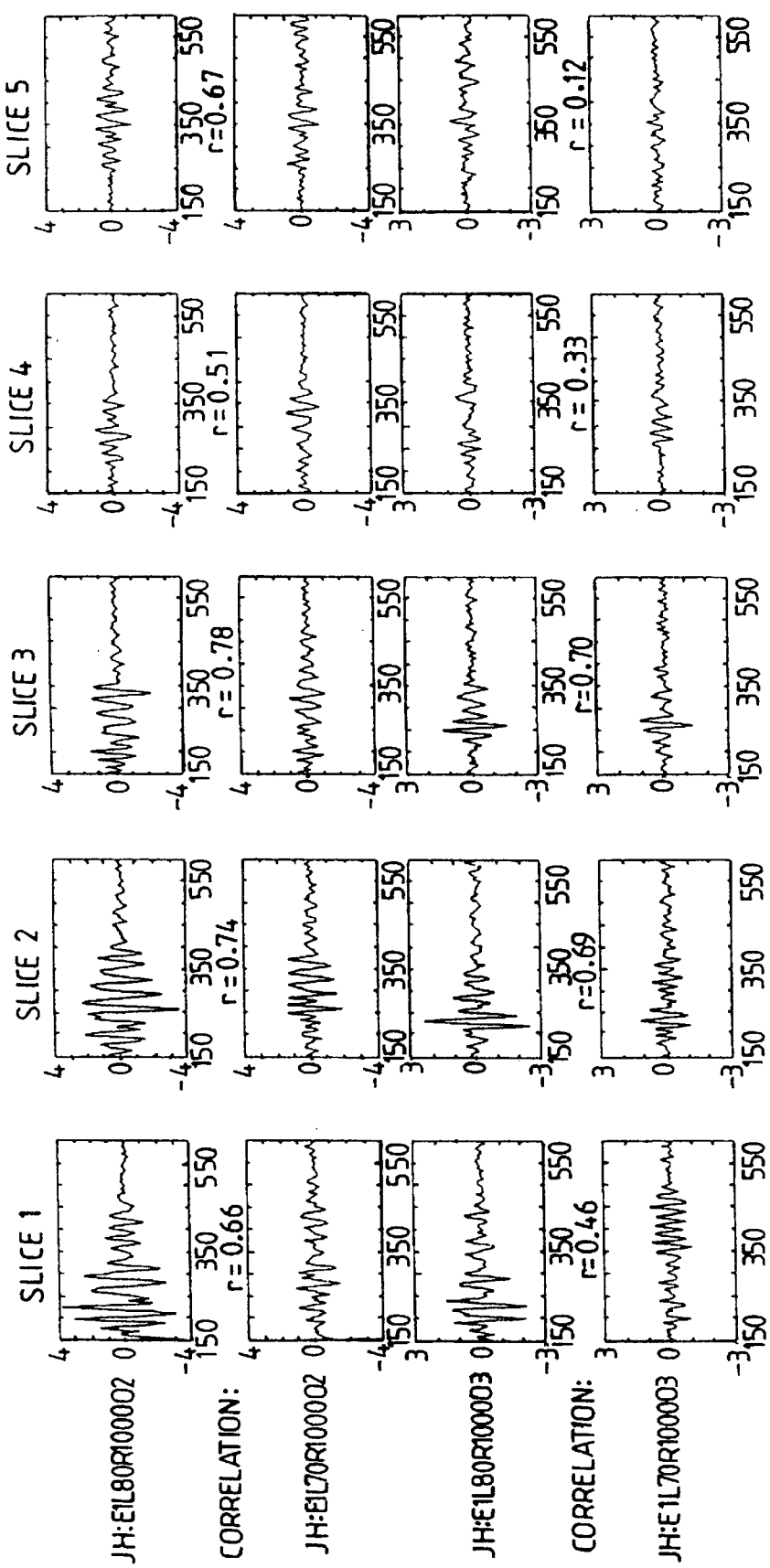

Effects of stimulus level are shown in FIG. 13. The top row shows the second order slices 1 to 5 recorded at 80 dB and, below that, the same slices at 70 dB stimulus level. There is a marked level effect. With the normal, linear component of the emission, there would be very little change at this stimulus level as we are on the saturating part of the input/output function. However, with these non-linear components there is a large change measurable with stimulus level. The same is true for the third order kernel slices shown in the bottom two lines. Nevertheless, there are reasonable correlations between the waveforms recorded at the sto stimulus levels. More so for the second order kernels than the third.

Figure 14:
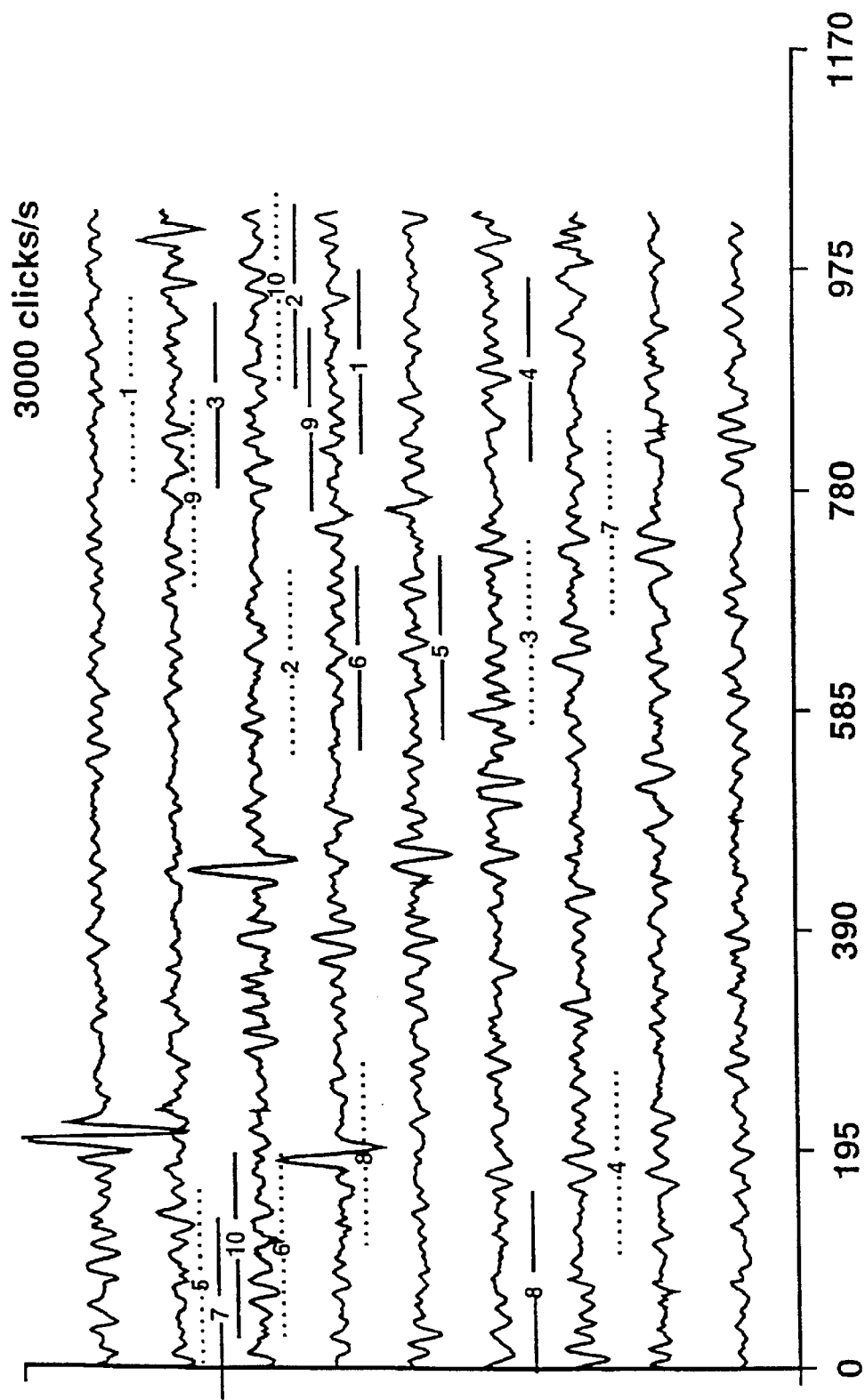

FIG. 14 shows the deconvolved MLS which is entire apart from the first 3000 points containing the normal, linear component. In this recording from a normally hearing subject, the dotted lines represent the slices of the second order kernel and the solid lines represent the slices of the third order kernel. This was for an MLS of order 10 containing 1023 click opportunities.

There are two things to be noted here. First of all there is still a great deal of overlap between some of the kernel slices and therefore we need to move to larger MLSs in order to avoid this. The second thing to note is that there are many components present outside the windows indicating the second and third order kernel slices. Thus not only are Volterra kernels of the second and third order present, but the ear is producing a rich harvest of even higher order components.

Figure 15:
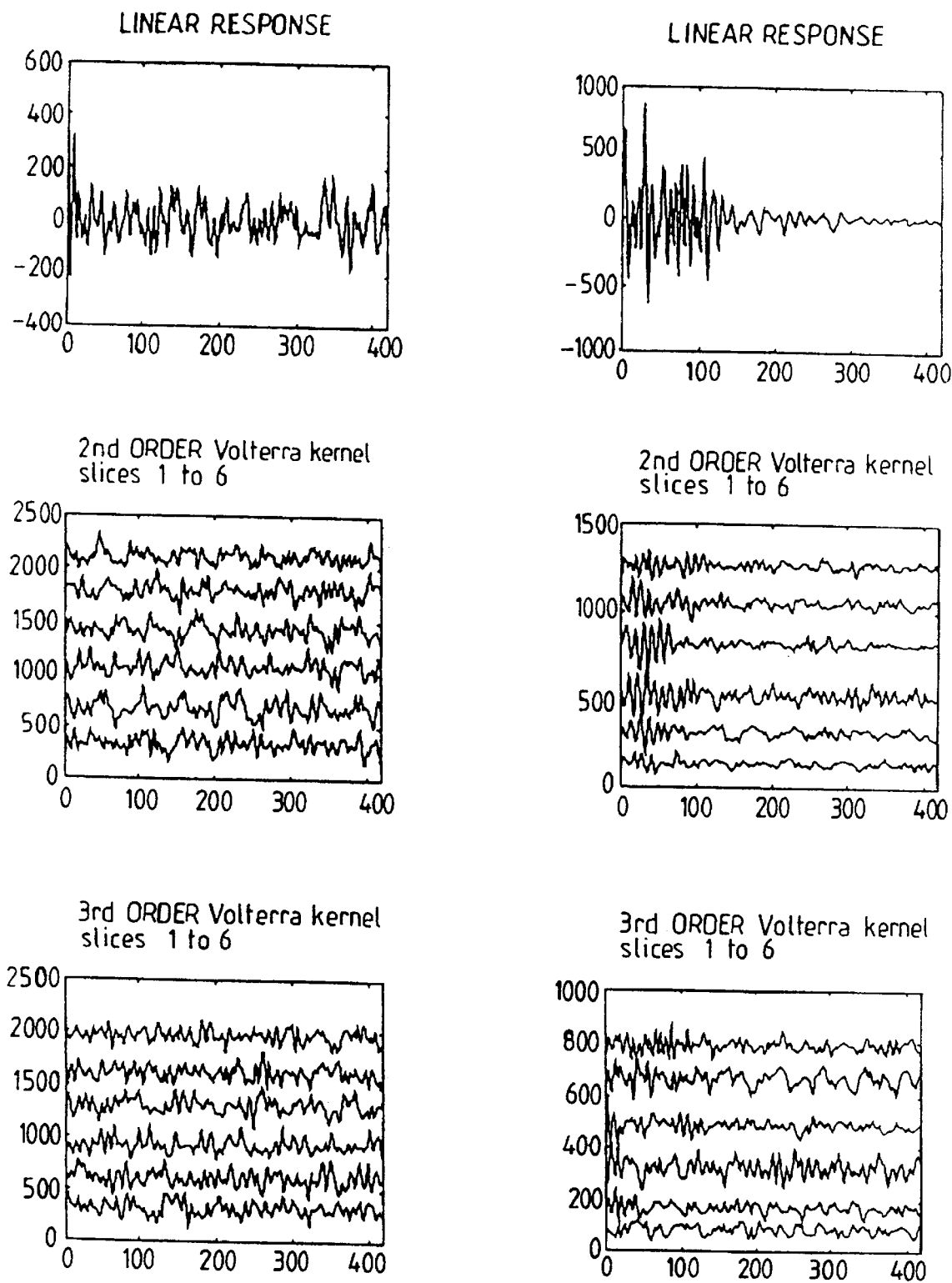

Data from a newborn baby are shown in FIG. 15. There are no clear linear nor Volterra kernel slices visible at age 3 hours 15 minutes (left-hand diagrams). However, both the linear and the Volterra kernel slices can clearly be seen in the recordings taken when the baby was aged 22 hours 45 minutes (right-handed diagrams). It is known that the amplitude of the linear component increases markedly during the first three days of life and it would appear that there is a similar maturational effect for the Volterra kernel slices.

These data have demonstrated that Volterra kernel slices of OAEs are real, physiological events. They are consistent, repeatable responses associated with the hearing process which are found both in adults and in babies.

Thus, a system of on-the-fly recovery of responses generated by an MLS has been disclosed. This permits the rejection of artefact-contaminated epochs and hence improves the signal-to-noise ratio. The advantages of speed and sensitivity can be realised for the linear component of the response.

What is claimed is:

1. A method of obtaining evoked otoacoustic emission (EOAE) response data, comprising:

generating a variant of a standard MLS wherein the −1s and +1s in the standard MLS are replaced by +1s and 0s respectively in the variant, using the variant MLS as stimulus signals, sensing response signals to the stimulus signals, deconvolving the stimulus and response signals in real time as the variant MLS is being generated in order to provide a deconvolved MLS waveform, detecting in the deconvolved MLS waveform non-linear temporal interaction components (NLTICs), and recording the NLTICs as slices through higher order Volterra Kernels with each Volterra Kernel representing a term in a Volterra series which models the stimulus/response system.

2. A method according to claim 1, wherein the higher order Volterra Kernels are at least the second and third order components of the Volterra series.

3. A method according to claim 1, wherein, for each investigated order of MLS, all possible MLSs are generated, the location of the NLTICs computed, and the optimum MLS, giving minimum overlap of the NLTICs with one another and with the linear component, selected.

4. A method according to claim 3, wherein the MLSs are software implemented.

5. A method according to claim 1, wherein the position of each slice in the deconvolved MLS is computed to enable its unique identification.

6. A method according to claim 1, wherein a rejection template to detect noisy epochs is applied to the deconvolved waveform obtained at the end of each successive MLS.

7. A method according to claim 6, wherein, for each MLS, a stimulus sequence s(n) and a recovery sequence r(n) are defined, and the two sequences cross-correlated.

* * * * *